(12) United States Patent
Mathew et al.

(10) Patent No.: US 8,955,388 B2
(45) Date of Patent: Feb. 17, 2015

(54) MOLD COMPOUND COMPATIBILITY TEST SYSTEM AND METHODS THEREOF

(75) Inventors: Varughese Mathew, Austin, TX (US); Sheila F. Chopin, Round Rock, TX (US); Leo M. Higgins, III, Austin, TX (US)

(73) Assignee: Freescale Semiconductor, Inc., Austin, TX (US)

( * ) Notice: Subject to any disclaimer, the term of this patent is extended or adjusted under 35 U.S.C. 154(b) by 255 days.

(21) Appl. No.: 13/484,353

(22) Filed: May 31, 2012

(65) Prior Publication Data

US 2013/0319129 A1    Dec. 5, 2013

(51) Int. Cl.
*G01N 3/08* (2006.01)
(52) U.S. Cl.
USPC ........................................................ 73/827
(58) Field of Classification Search
USPC ........................................................ 73/827
See application file for complete search history.

(56) References Cited

U.S. PATENT DOCUMENTS

| | | | | |
|---|---|---|---|---|
| 3,384,680 A | * | 5/1968 | Lussow | 528/92 |
| 6,046,507 A | * | 4/2000 | Hatchard et al. | 257/790 |
| 8,404,520 B1 | * | 3/2013 | Chau et al. | 438/109 |
| 8,513,771 B2 | * | 8/2013 | Elian et al. | 257/531 |
| 8,525,305 B1 | * | 9/2013 | Rogren | 257/666 |
| 8,618,659 B2 | * | 12/2013 | Sato et al. | 257/737 |

OTHER PUBLICATIONS

Lee, C. et al., "Challenges of Cu Wire Bonding on Low-k/Cu Wafers with BOA Structures," IEEE 2010 Electronic Components and Technology Conference; Jun. 1-4, 2010; pp. 342-349.

Gan, C.L. et al., "Environmental Friendly Package Development by Using Copper Wirebonding," 34th International Electronic Manufacturing Technology Conference, 2010; Nov. 30, 2010-Dec. 2, 2010; 5 pages.

Tran, T.A., et al., "Copper Wire Bonding on Low-k/Copper Wafers with Bond Over Active (BOA) Structures for Automotive Customers," 2011 Electronic Components and Technology Conference; May 31, 2011-Jun. 3, 2011; pp. 1508-1515.

* cited by examiner

*Primary Examiner* — Lisa Caputo
*Assistant Examiner* — Octavia Hollington (57) ABSTRACT

A technique for testing the compatibility of an encapsulation material and a wire bond included at an unencapsulated assembly. The technique includes immersing the assembly in an encapsulating compound extract. The assembly includes a semiconductor die and a bonding wire affixed to a metalized pad of the semiconductor die by the wire bond. After the immersing, a mechanical strength of the wire bond is determined.

20 Claims, 5 Drawing Sheets

MOLD COMPOUND COMPATIBILITY TEST SYSTEM AND METHODS THEREOF

FIELD OF THE DISCLOSURE

The present disclosure relates generally to semiconductor die, and more particularly to packaging of semiconductor die.

BACKGROUND

A semiconductor die is manufactured using photolithographic techniques wherein circuit elements, including transistors, are fabricated at a semiconductor substrate. Various processes are used to form metal features to provide electrical interconnections between corresponding circuit elements. Other metal features provide terminals for communicating signals into and out of the integrated circuit. A semiconductor die is structurally fragile and typically requires protection from environmental contaminants, including moisture. Therefore, a semiconductor die is generally incorporated into a device package that protects the die and that facilities installation of the die into a manufactured product. For example, a semiconductor die can be encapsulated within a plastic compound.

BRIEF DESCRIPTION OF THE DRAWINGS

The present disclosure may be better understood, and its numerous features and advantages made apparent to those skilled in the art by referencing the accompanying drawings.

DETAILED DESCRIPTION

FIGS. 1-7 illustrate a system and method for evaluating the suitability of a semiconductor die encapsulation material. An encapsulation material, such as a mold compound, may be incompatible with components included at an integrated circuit substrate/die assembly. For example, a particular mold compound may be excessively corrosive to materials used to fabricate the integrated circuit device. Corrosion can impair the electrical and mechanical performance of an integrated circuit device, and can reduce the reliability or operating lifetime of the device. Corrosion can be especially detrimental to Copper and Aluminum metals associated with wire bonds, and the intermetallic bond phase or phases that forms between these two metals, that provide an electrical interconnection between terminal pads of an integrated circuit die and corresponding terminals of an associated package substrate. Techniques described herein can be used to determine whether a mold compound adversely affects the operation and reliability of an integrated circuit device. For example, a mechanical strength of a wire bond included at a substrate/die assembly can be evaluated after exposing an unencapsulated substrate/die assembly to a mold compound extract. The bonding strength of the wire bond that has been exposed to the extract can be compared to a bonding strength of a wire bond at an assembly that has not been exposed to the encapsulating compound extract to identify whether the strength of a wire bond is adversely affected by the encapsulating compound. A semiconductor die can include an integrated circuit die, a transistor die, and the like. For clarity, the following description refers to an integrated circuit die, but is applicable to any semiconductor die.

An integrated circuit device generally includes an integrated circuit die incorporated within a structural carrier known as an integrated circuit package. Many different packaging technologies are in use today. A common type of integrated circuit package includes a substrate upon which an integrated circuit die is attached. The substrate/die assembly is at least partially encapsulated in an encapsulating compound to isolate the integrated circuit die from the environment and to provide a structural foundation for electrical terminals used to carry signals to and from the integrated circuit die. As used herein, a substrate can include a patterned substrate, an interposer, a build-up substrate, a metal lead frame, or another type of structure for communicating signals between the input/output terminals of an integrated circuit die and corresponding terminals of an integrated circuit package. For example, a patterned substrate can include an insulating material upon which metal features are disposed, while a lead frame can include metal features without an insulating component. One method for communicating signals between an integrated circuit die and the substrate is to provide bonding wires between bond pads at the integrated circuit die and corresponding lands at the substrate. One technique for attaching a bonding wire to an integrated circuit die is by means of a wire ball bond. A wire ball bond is created using electrical energy, thermal energy, ultrasonic energy, or a combination thereof to substantially weld the bond wire to the metal bond pad of the integrated circuit die. Other wire bonding techniques include wedge bonding, ribbon bonding, and the like.

Bonding wires have historically been made out of gold metal due to favorable mechanical, electrical and chemical properties of gold. Today, Copper bonding wire is becoming more common. Copper has good electrical properties and is more economical than gold. A bond pad provided at an integrated circuit die to which the bonding wire is attached is typically Aluminum or an Aluminum alloy. Bond wires can include other conductive materials, for example Aluminum, Palladium-coated Copper, Palladium doped Copper, polymer coated metal, and the like. Similarly, a bond pad can include other conductive materials, such as copper. In an embodiment, the bonding wire and bond pad can include substantially the same material. For example, a bond pad and a corresponding bond wire can include Copper metal. The metal lands included at the patterned substrate can be Copper, Copper plated with nickel and then gold, Copper plated with silver or tin, or another metal material. One issue that arises with the use of Copper bonding wire is corrosion that can occur at the interface of the Copper bond wire and the Aluminum feature of the integrated circuit die. Corrosion at a Copper-Aluminum interface can be aggravated by the presence of a mold compound or other compound used to encapsulate the substrate/die assembly. For example, an encapsulation compound may include chemical ions that can migrate or leach from the mold compound to the metal features due to the presence of minute amounts of water present in the cured encapsulation material. For the purpose of example, the term mold compound is used herein to represent any encapsulation material. As used herein, the term Copper is used to refer to substantially pure Copper metal or to refer to metal alloys where Copper metal is the majority constituent. Similarly, the term Aluminum is used to refer to Aluminum or an Aluminum alloy.

Figure 1:
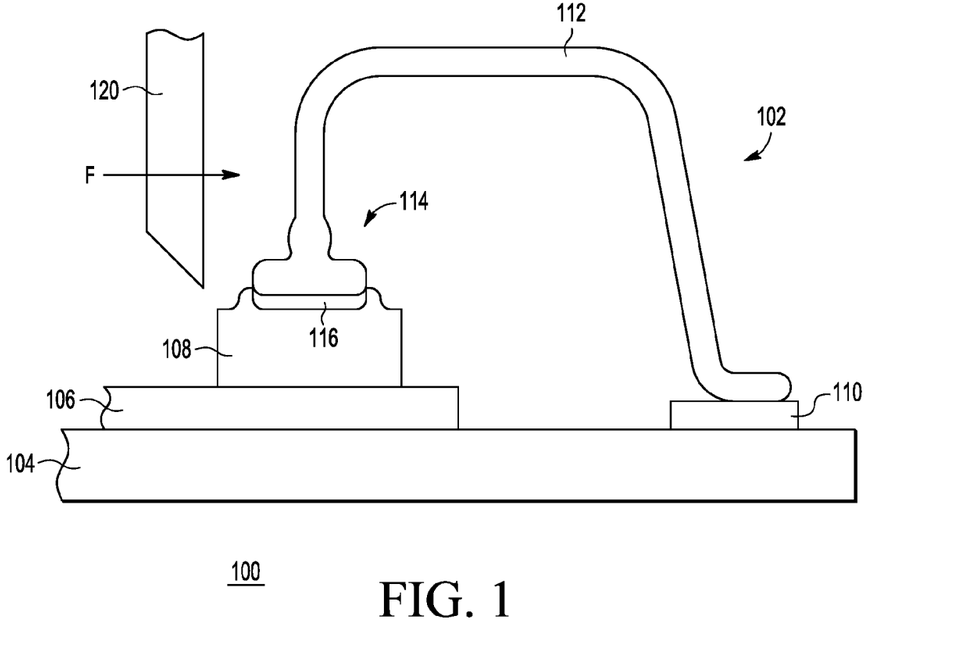
FIG. 1 is a cross sectional side view of a portion of a test system for identifying adverse effects of a mold compound on wire bonds at an integrated circuit device in accordance with a specific embodiment of the present disclosure.

FIG. 1 is a cross sectional side view of a test system 100 for identifying adverse effects of a mold compound on wire bonds at an integrated circuit device in accordance with a specific embodiment of the present disclosure. The test system includes a substrate/die assembly 102 and a force applicator 120. The substrate/die assembly 102 includes a patterned substrate 104, an integrated circuit die 106, a bond pad 108, a substrate land 110, and a bond wire 112 including a wire ball bond 114 and an intermetallic region 116. The substrate/die assembly 102 represents an intermediate stage in the production of an integrated circuit device. In particular, the assembly 102 can represent the device prior to encapsulation in a mold compound. In an embodiment the substrate/die assembly 102 has been exposed to a mold compound extract. For clarity, features illustrated at the test system 100 and at the substrate/die assembly are not drawn to scale. Actual dimensions can vary considerably, however a typical bond wire can be twenty-three micrometers in diameter and a typical wire ball bond can be forty-five micrometers in diameter. The intermetallic region 116 can include more than one chemical compound. For example, a Copper bonding wire affixed to an Aluminum bonding pad can include $Cu_9Al_4$, $Cu_2Al$, $CuAl$, other intermetallic phases, or a combination thereof. Some types of intermetallic compounds, such as Copper-rich phases, may be more readily corroded by a mold compound than other phases.

During operation of the test system 100, the force applicator 120 applies a successively increasing amount of force to the ball bond until destructive failure of the bond occurs. The force necessary to sever the bond is recorded, and is herein referred to as the bond shear strength of the wire ball bond, or simply the wire bond strength. During operation, a force is applied by the force applicator 120 in a direction parallel to the planar surface of the integrated circuit die and against the side of the wire ball bond. A substrate/die assembly 102 typically includes many individual wire ball bonds corresponding to respective bond pads and bond wires. In an embodiment, bond shear strength of additional wire ball bonds can be determined in the same way described above, and any variations in the shear strength of each wire ball bond also can be determined.

In an alternative embodiment (not shown at FIG. 1), a force applicator can be configured to pull the bond wire 112 up and away from the surface of the integrated circuit die to determine a pull strength of the wire ball bond, or the breaking strength of the wire. In still another embodiment, the wire ball bond 114 can instead be another type of mechanical bond that provides a conductive connection such as a stitch bond or the like. The techniques disclosed herein are applicable to alternative wire bonds technologies and bond strength measurement techniques. However, for the purpose of example, the forgoing description is directed to bond shear strength of a wire ball bond. In an embodiment, the substrate/die assembly 102 can include an actual production unit diverted from a production line. In another embodiment, test procedures disclosed herein can be performed on a test die that is different from a marketed device. For example, a test of wire bond strength can be performed at a bond pad at a semiconductor die that does not include semiconductor devices.

Figure 2:
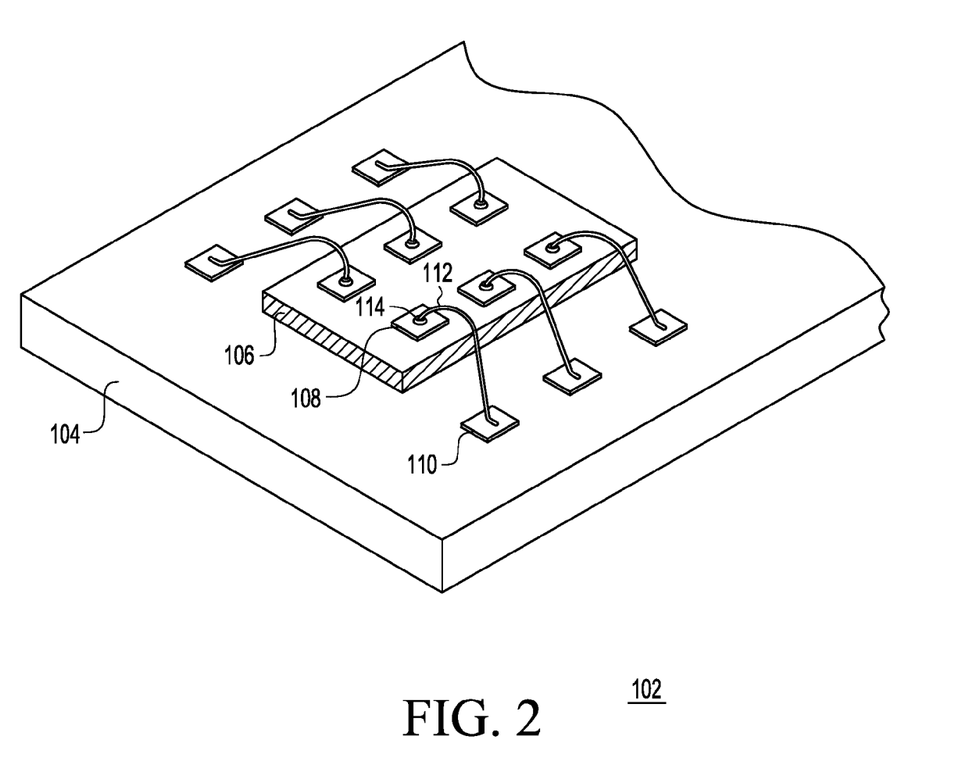
FIG. 2 is a perspective view of a substrate/die assembly of FIG. 1 in accordance with a specific embodiment of the present disclosure.

FIG. 2 is a perspective view of the substrate/die assembly 102 of FIG. 1 in accordance with a specific embodiment of the present disclosure. The substrate/die assembly 102 includes a patterned substrate 104, the integrated circuit die 106, the bond wire 112 affixed to the bond pad 108 by a wire ball bond 114 and affixed to the land 110 of the substrate. The patterned substrate 104 can include an organic material, a ceramic material, or another type of material that provides electrical insulation. The patterned substrate includes conductive lands, such as the land 110, to receive signals from the integrated circuit die 106 via bond wires, such as the bond wire 112. The patterned substrate can include multiple layers of insulating material and each layer can include corresponding metal interconnect features as well as conductive vias for communicating signals from one metal layer to another. The patterned substrate is similar to a printed circuit board in many respects. The substrate/die assembly shown at FIG. 2 has not yet been encapsulated in a mold compound. In an embodiment, a substrate can include replicated regions, each region to receive a respective integrated circuit die and providing corresponding lands and metal interconnect features. During the manufacturing process, an individual integrated circuit die can be attached to the substrate at each region and bonding wires can be provided to interconnect each die to corresponding substrate lands. The individual regions may be separated before or after encapsulation of each integrated circuit die, depending on the specific type of packaging technology employed. In another embodiment, a substrate/die assembly can include a lead frame. A lead frame (not shown at FIG. 2) is similar to the patterned substrate described above, but does not include insulating material, except for instances where a polymer film is adhesively bonded to the lead frame to provide mechanical support. Instead, metal features of the lead frame can be initially interconnected to provide a single work piece and excess portions of the lead frame can be trimmed during the assembly process, typically after encapsulation. As with the patterned substrate, bond wires communicate signals between lands at the lead frame and bond pads of a corresponding integrated circuit die, with the bond wire attached to the die using a wire bond.

Figure 3:
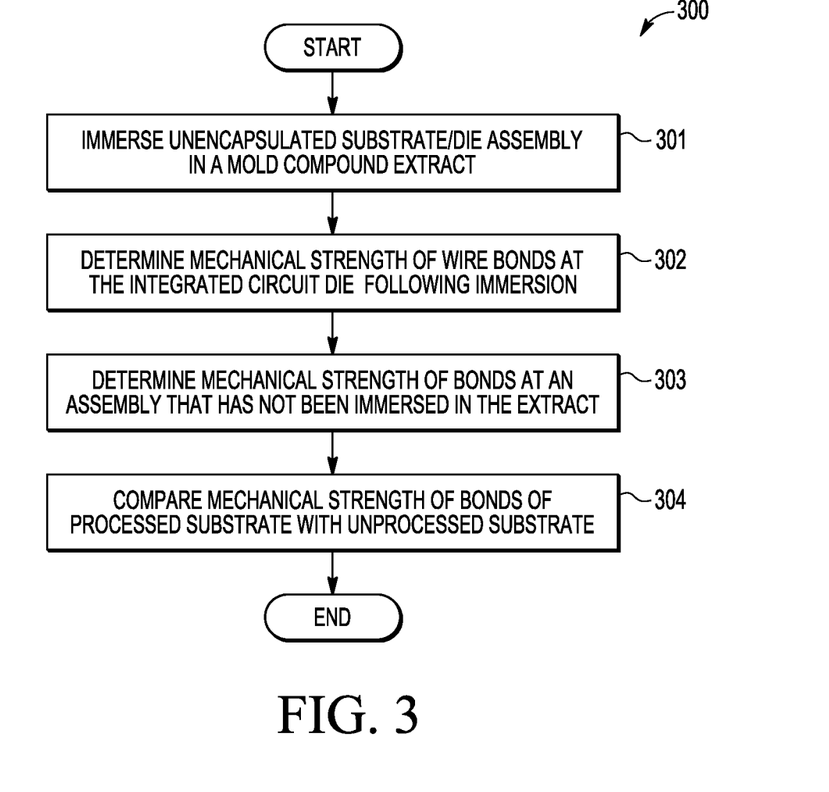
FIG. 3 is a flow diagram illustrating a method in accordance with a specific embodiment of the present disclosure.

FIG. 3 is a flow diagram illustrating a method 300 in accordance with a specific embodiment of the present disclosure. The method 300 describes determining a bond strength of a wire bond at an integrated circuit die after exposing a substrate/die assembly, such as the substrate/die assembly 102 of FIG. 1 and FIG. 2, to a mold compound extract. The flow begins at block 301 where an unencapsulated substrate/die assembly is immersed in a mold compound extract. A mold compound extract can be prepared from a mold compound as described below. The substrate/die assembly can be exposed to the mold compound extract for a predetermined period of time. In an embodiment, the substrate/die assembly and the extract can be maintained at an elevated temperature for the duration of the immersion procedure. For example, a substrate/die assembly, such as the substrate/die assembly 102, can be submerged in a quantity of mold compound extract solution within a vessel secured to prevent evaporation, and the vessel can be heated using a water bath, an oven, a hot-plate, or the like. The temperature can be maintained for the predetermined amount of time. The vessel can be periodically or continuously agitated during the immersion procedure. The immersion procedure is described in detail below with reference to FIGS. 4 and 5.

The flow proceeds to block 302 where a mechanical strength of one or more wire bonds at the integrated circuit die is determined following the immersion. For example, the test system 100 of FIG. 1 can be used to determine shear strength of wire ball bonds using a force applicator, such as the force applicator 120. Shear strength represents an amount of force required to destructively sever a wire bond, for example to break the connection between the bond wire and bond pad of the integrated circuit die. Shear strength can be represented by a force, expressed in Newtons or the like. Shear strength can also be expressed using units of mass, such as grams, wherein standard gravitational acceleration is implied. For example, the shear strength of a wire bond, such as the wire ball bond 114 of FIG. 1 can be determined to be twenty grams (0.02 kilograms). Formally, this quantity represents a minimum force of (0.02×g Newtons) that is required to sever the wire bond.

The shear strength information can be stored in a database or plotted graphically. Strength information associated with multiple wire bonds can be analyzed to determine a minimum strength, a maximum strength, a mean strength, deviation from the mean, and the like. The flow proceeds to block 303 where a mechanical strength of bonds at an assembly that has not been immersed in the mold compound extract is determined. For example, a substrate/die assembly that is otherwise identical to the extract-processed assembly of block 302, can undergo the same testing procedure described above. The flow proceeds to block 304 where the mechanical strengths of the bonds on the processed substrate are compared to the strengths of the bonds at the unprocessed assembly. If the strength of the bonds at the processed assembly is statistically below those of the unprocessed assembly, there is an indication that chemicals present in the mold compound have corroded or otherwise adversely affected the bond between the bond wire 112 and the bond pad 108 of the integrated circuit die. For example, if the average shear strength of fifty wire bonds of a substrate/die assembly that has been exposed to mold compound extract is fifteen grams, and the average shear strength of another set of wire bonds of a substrate/die assembly that has not been exposed to the mold compound extract is twenty grams, there is evidence that the mold compound extract may include chemicals that weakened the wire bond. A large sample size can increase the statistical accuracy of the test results by minimizing the effects of other manufacturing and testing variations.

Figure 4:
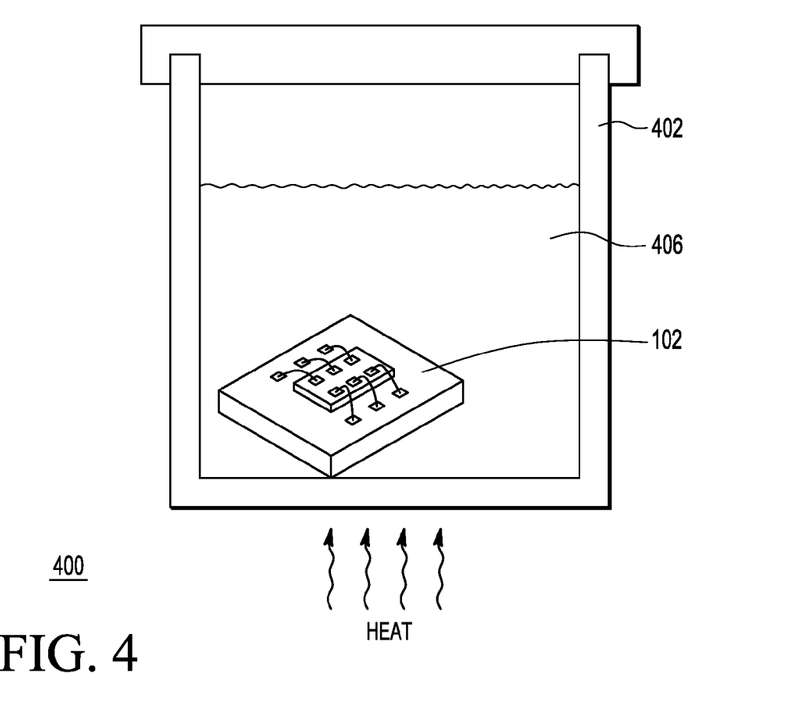
FIG. 4 includes a cut-away side view of an apparatus for immersing a substrate/die assembly in a mold compound extract in accordance with a specific embodiment of the present disclosure.

FIG. 4 includes a cut-away side view of an apparatus 400 for immersing a substrate/die assembly in an encapsulating compound extract, such as a mold compound extract in accordance with a specific embodiment of the present disclosure. The apparatus 400 includes a containment vessel 402 capable of withstanding heat. In an embodiment, the vessel can be sealable and be capable of maintaining a pressure inside the vessel that is greater than ambient atmospheric pressure when heated for an extended period of time. Such a vessel may be referred to as a bomb. A substrate/die assembly, such as the substrate/die assembly 102, is placed inside the bomb and a quantity of mold compound extract 406 is added to the vessel to submerge the assembly. The lid of vessel 402 is attached and appropriate retaining devices and seals (not shown at FIG. 4) are activated to seal the vessel. The vessel can be made of a substantially inert material, such as Polytetrafluoroethylene (PTFE), high-purity glass, ceramic, stainless steel, or another material capable of withstanding an elevated temperature and pressure and does not leach corrosive anions into the extract solution. In an embodiment, heat is applied to the vessel for a predetermined amount of time. For example, the vessel can be maintained at a temperature of 75° C. to 85° C. for a period of between 25-175 hours. A preferred temperature and immersion duration can be selected based on experimentation to provide a desired acceleration of corrosion processes that may occur at the wire bonds in response to normal exposure of the wire bond to the mold compound extract. For example, a sealed vessel can be maintained at a temperature in excess of 100° C.

Figure 5:
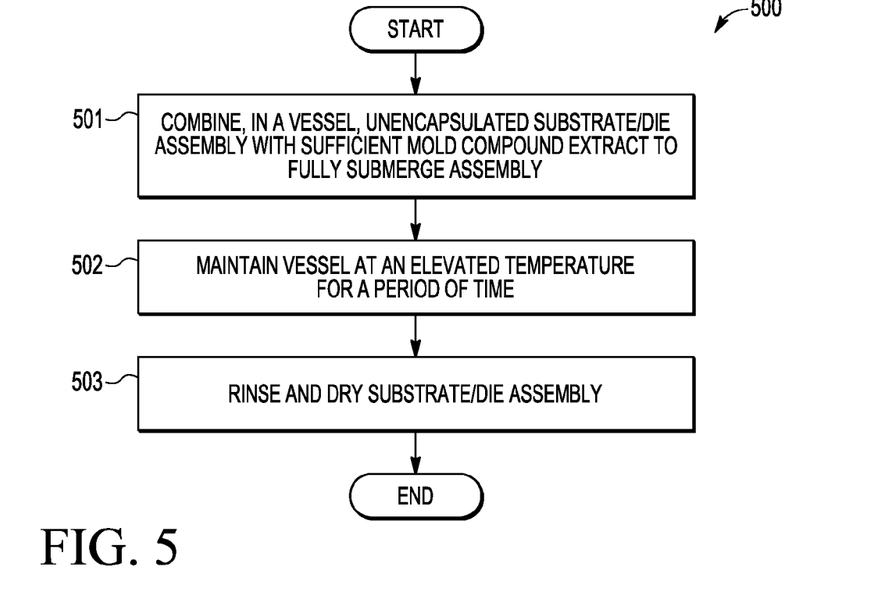
FIG. 5 is a flow diagram illustrating a method for subjecting a substrate/die assembly to a mold compound extract in accordance with a specific embodiment of the present disclosure.

FIG. 5 is a flow diagram illustrating a method 500 for subjecting a substrate/die assembly to a mold compound extract in accordance with a specific embodiment of the present disclosure. The method 500 begins at block 501 where an unencapsulated substrate/die assembly is combined in a sealable vessel with sufficient mold compound extract to submerge the assembly. For example, the substrate/die assembly 102 can be inserted into the vessel 402 described above, and a quantity of mold compound extract adequate to envelope all of the wire bonds included on the assembly can be added to the vessel 402. The method proceeds to block 502 where the vessel is sealed and maintained at an elevated temperature for a period of time. As described above, the elevated temperature is selected to accelerate any chemical reactions that may occur between chemicals present in the mold compound extract and the metals associated with the wire bond. These chemical reactions are expected to occur at a slower rate within an encapsulated integrated circuit device. In an embodiment, it may be determined that mere soaking at room temperature, without additional applied heat, provides an adequate environment for corrosion to take place. For example, the substrate/die assembly can be immersed for a longer period of time to compensate for the lack of an elevated temperature. In an embodiment, an electrical potential can be applied to portions of the substrate/die assembly to provide an electrical current that flows through the wire bond. In another embodiment, an electrochemical cell can be formed by applying an anodic connection to power to every other ball bond and a cathodic connection to ground on the remaining ball bonds. In still another embodiment, all of the ball bonds can be anodically connected to power and a cathode can be immersed in the extract adjacent to the substrate/die assembly.

The flow proceeds to block 503 where the substrate/die assembly is removed from the vessel, rinsed, and dried. For example, the substrate/die assembly can be rinsed with purified water to remove chemicals deposited on the assembly by the mold compound extract solution. In addition, the assembly can be dried using pressurized air, dry nitrogen gas, or the like. The method 500 can be repeated for additional substrate/die assemblies to provide additional devices for testing. Alternatively, multiple assemblies can be processed simultaneously in a single vessel of suitable size. Testing of a greater number of thusly-processed wire bonds can increase the statistical accuracy of test results.

Figure 6:
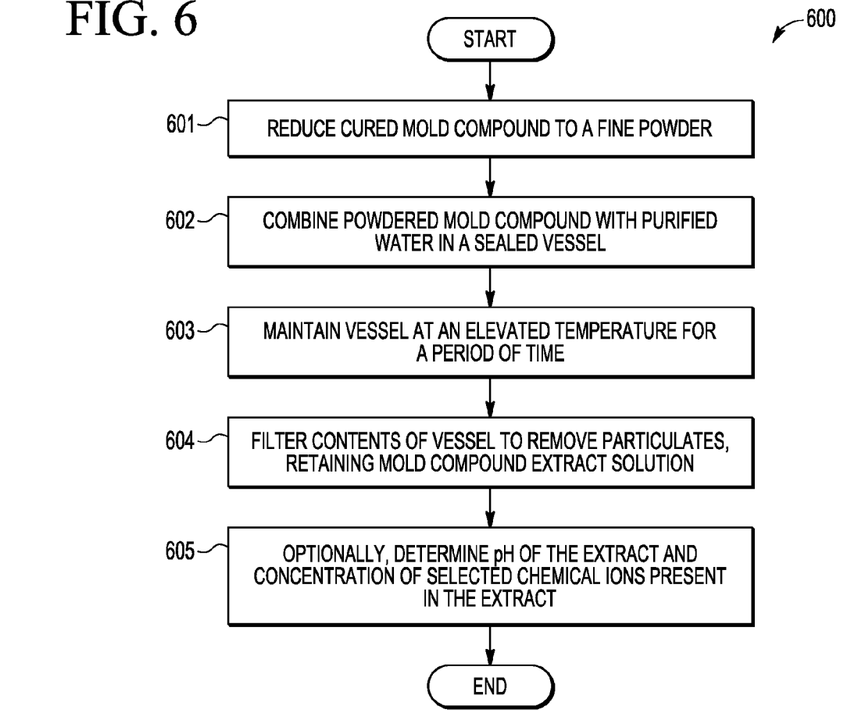
FIG. 6 illustrates a method for preparing a mold compound extract in accordance with a specific embodiment of the present disclosure.

FIG. 6 illustrates a method 600 for preparing a mold compound extract in accordance with a specific embodiment of the present disclosure. The method 600 generally facilitates extraction (leaching) of water soluble chemicals and/or chemical ions from a cured mold compound. The flow begins at block 601 where cured mold compound is reduced to a fine powder. Mold compound generally includes two or more chemical components, which when combined and processed, hardens into a solid mass. The process of hardening can be referred to as curing. Accordingly, mold compound that has undergone the curing process is referred to herein as cured mold compound. In an embodiment, the mold compound can include an epoxy and the constituent components can include an epoxy resin and a hardener. In another embodiment, the mold compound can include a thermoplastic, a sealant, Silicone, an elastomer, or another type of material suitable for encapsulating an integrated circuit die at a substrate/die assembly. The mold compound also may include filler or bulking materials such as powdered glass, crushed silica, spherical fused silica, or the like. The cured mold compound can be reduced to a fine powder by any suitable means, including ball milling, rotary milling, abrasion, and the like. In an embodiment, the resulting powder has a maximum particle size of ten micrometers or less, however, a coarser or finer particle size can be used. A finer particle size can permit chemical ions contained therein to be extracted more readily.

The flow proceeds to block 602 where the powdered mold compound is combined with purified water in a vessel and the vessel is sealed. For example, five grams of powdered mold compound can be combined with fifty grams of purified water. The purified water can include distilled water, ultra-pure water, or the like. The ratio of powdered mold compound to water can vary as desired. For example, a greater quantity of powdered mold compound in relation to a quantity of water can result in a mold compound extract that contains a greater concentration of ions. The flow proceeds to block 603 where the sealed vessel is maintained at an elevated temperature for a period of time. A temperature between 100° C. and 200° C., and preferably between 120° C. and 130° C. is recommended. For example, the vessel can be heated to 121° C. for several hours. Generally, the extraction process can be made more complete if the vessel is maintained at the elevated temperature for a longer period of time or if the vessel is maintained at a greater temperature. Because the temperature of 121° C. exceeds the boiling point of water, pressure within the sealed vessel can rise above atmospheric pressure. In an embodiment, the contents can be stirred or otherwise agitated during all or a portion of the time the extract is being prepared.

The flow proceeds to block 604 where the contents of the vessel is filtered to remove undissolved particulates of cured mold compound while retaining the liquid mold compound extract solution. For example, high purity filter paper can be used with a funnel, such as a Buchner funnel or the like, to separate the desired mold compound extract from the powdered cured mold compound. The flow proceeds to block 605 where, optionally, the pH and the concentration of selected chemicals or chemical ions present in the extract can be determined. For example, chemical, spectrographic, or another type of qualitative or quantitative analysis can be used to determine the presence or the concentrations of dissolved species which may include inorganic and organic ions, and non-ionized dissolved species present in the extract. For example, the mold compound extract can include chemicals or ions such as chloride, formate, acetate, oxalate, ammonia, anions, cations, other dissolved species, and the like. In an embodiment, the pH and/or the chemical composition of the extract may be empirically correlated with bond strength test results determined using substrate/die assemblies that have been exposed to the mold compound extract.

Figure 7:
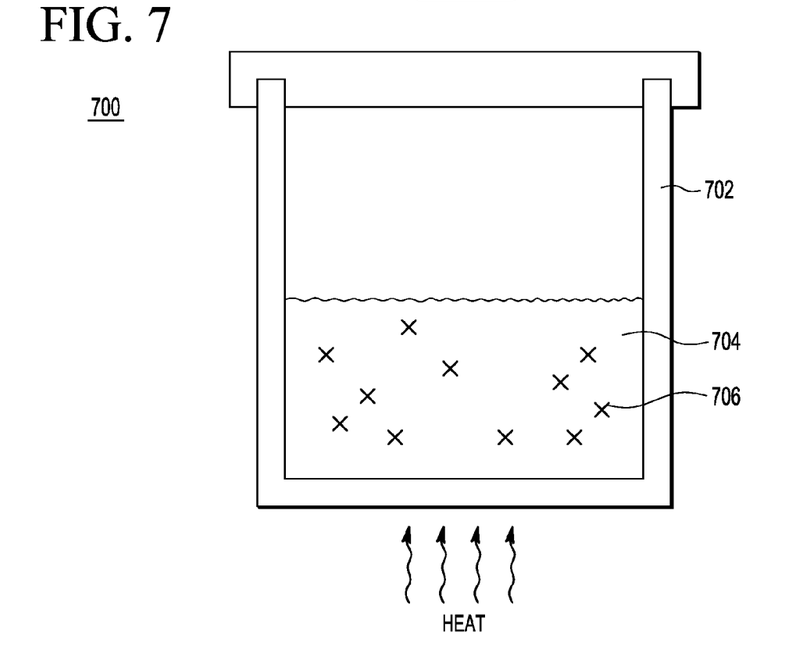
FIG. 7 is a cut-away side view illustrating an apparatus for preparing a mold compound extract in accordance with a specific embodiment of the present disclosure.

FIG. 7 is a cut-away side view illustrating an apparatus 700 for preparing a mold compound extract in accordance with a specific embodiment of the present disclosure. The apparatus can be similar to the apparatus described above with reference to FIG. 4. The apparatus 700 includes a sealable containment vessel 702. The vessel 702 can be similar to the vessel 402, and may include a bomb or another container able to withstand elevated temperatures and pressures. Like the vessel 402, the vessel 702 is, ideally, substantially chemically inert so as to not significantly contaminate the extract being prepared with chemical components associated with the vessel.

The apparatus includes purified water 704 and powdered mold compound 706 as described above with reference to method 600.

In an embodiment, the suitability of a mold compound can be determined using the techniques described herein each time a new shipment or production lot of mold compound is received at a manufacturing operation, or when a new supplier of mold compound is evaluated. Similarly, the disclosed compatibility tests can be performed if processes or materials used in the manufacture of the integrated circuit die or the substrate/die assembly is altered. For example, a new type of bond wire or a new type of wire bonding apparatus can expose new mold compound compatibility issues.

In this document, relational terms such as "first" and "second", and the like, may be used solely to distinguish one entity or action from another entity or action without necessarily requiring or implying any actual relationship or order between such entities or actions or any actual relationship or order between such entities and claimed elements. The term "another", as used herein, is defined as at least a second or more. The terms "including", "having", or any variation thereof, as used herein, are defined as comprising.

Other embodiments, uses, and advantages of the disclosure will be apparent to those skilled in the art from consideration of the specification and practice of the disclosure disclosed herein. The specification and drawings should be considered as examples only, and the scope of the disclosure is accordingly intended to be limited only by the following claims and equivalents thereof.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed.

Also, the concepts have been described with reference to specific embodiments. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

What is claimed is:

1. A method comprising:
   immersing a first unencapsulated assembly in an encapsulating compound extract prepared using an encapsulating compound, the assembly including a semiconductor die having a bond pad affixed to a bonding wire by a first wire bond;
   removing the first unencapsulated assembly from the encapsulating compound extract; and
   determining a mechanical bond strength of the first wire bond subsequent to immersing.

2. The method of claim 1, wherein the unencapsulated assembly includes a substrate at which the semiconductor die is attached.

3. The method of claim 1 further comprising:
  determining a mechanical bond strength of a second wire bond at a second unencapsulated assembly, the second assembly having not been immersed in the encapsulating compound extract; and
  comparing the mechanical bond strength of the first wire bond to the mechanical bond strength of the second wire bond.

4. The method of claim 1 further comprising:
  determining a mechanical strength of a second wire bond at the first assembly; and
  comparing the mechanical bond strength of the first wire bond to the mechanical bond strength of the second wire bond.

5. The method of claim 1 wherein the first wire bond is a wire ball bond.

6. The method of claim 1 wherein the bonding wire comprises Copper.

7. The method of claim 1 wherein the bond pad comprises Aluminum.

8. The method of claim 1, further comprising:
  mixing purified water and powdered cured encapsulating compound to form the encapsulating compound extract.

9. The method of claim 1, further comprising:
  mixing purified water and powdered cured encapsulating compound; and
  filtering the mixture and retaining an aqueous extract free from undissolved solids.

10. The method of claim 1, wherein preparation of the encapsulating compound extract comprises:
  heating a mixture of purified water and powdered cured encapsulating compound.

11. The method of claim 1, wherein preparation of the encapsulating compound extract comprises:
  heating a mixture of purified water and powdered cured encapsulating compound; and
  filtering the mixture subsequent to heating and retaining an aqueous extract free from undissolved solids.

12. The method of claim 1 further comprising:
  determining an encapsulating compound corresponding to the encapsulating compound extract is suitable for encapsulating assemblies based on determining the mechanical bond strength.

13. The method of claim 1 wherein determining a mechanical bond strength comprises determining a bond shear strength of the first wire bond, the shear strength representative of an amount of force, applied to the wire bond in a direction parallel to the surface of the semiconductor die, necessary to destructively sever the first wire bond.

14. The method of claim 1 further comprising determining a concentration of each of a plurality of ions present in the encapsulating compound extract.

15. The method of claim 1 further comprising providing an electrical potential to the first wire bond during the immersing.

16. A system comprising:
  a test fixture;
  a first unencapsulated assembly including an integrated circuit die, a bonding wire affixed to a bond pad of the integrated circuit die by a first wire bond, and wherein the first assembly has been exposed to an encapsulating compound extract;
  a force applicator for providing a force to the wire bond; and
  a gauge for determining an amount of force necessary to destructively separate the bond wire from the bond pad.

17. A method comprising:
  determining a mechanical strength of each of a plurality of wire bonds included at a first set and at a second set of unencapsulated assemblies, each assembly including a semiconductor die and a bonding wire affixed to a bond pad of the semiconductor die by a corresponding wire bond, wherein the first set of assemblies has been exposed to an encapsulating compound extract and the second set of assemblies has not been exposed to the encapsulating compound extract; and
  comparing the mechanical strength of the wire bonds at the first set to the mechanical strength of the wire bonds at the second set.

18. The method of claim 17 further comprising determining that the encapsulating compound used to prepare the encapsulating compound extract is incompatible with materials associated with the wire bonds in response to determining that the average mechanical strength of the wire bonds of the first set is less than the average mechanical strength of wire bonds of the second set by a predetermined amount.

19. The method of claim 17 further comprising determining a concentration of each of a plurality of ions present in the encapsulating compound extract.

20. The method of claim 17 further comprising determining a pH of the encapsulating compound extract.

\* \* \* \* \*